US00PP33180P2

(12) United States Plant Patent
Pineau

(10) Patent No.: US PP33,180 P2
(45) Date of Patent: Jun. 22, 2021

(54) ***HIBISCUS* PLANT NAMED 'MINSYBV3S01'**

(50) Latin Name: *Hibiscus syriacus*
Varietal Denomination: MINSYBV3S01

(71) Applicant: Hortival Diffusion SAS, Beaufort en Vallee (FR)

(72) Inventor: Patrick Pineau, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 96 days.

(21) Appl. No.: 16/602,747

(22) Filed: Dec. 3, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Hibiscus* plant named 'MINSYBV3S01' is disclosed, characterized by large violet-blue flowers having a small maroon eye. Plants are well branched and upright. The new variety is a *Hibiscus*, normally produced as an outdoor garden or container plant.

2 Drawing Sheets

Latin name of the genus and species: *Hibiscus syriacus*.
Variety denomination: 'MINSYBV3S01'.

BACKGROUND OF THE INVENTION

The new *Hibiscus* cultivar is a product of a planned breeding program conducted by the inventor, Patrick Pineau. The objective of the breeding program was to produce new flower colors. The cross resulting in this new variety was made in July 2007.

The seed parent is an unnamed, unpatented *Hibiscus* seedling from advanced internal selection '#11647'. The pollen parent is unknown, as this was the result of open pollination. The new variety was identified and selected as a potentially interesting selection in October 2010. Selection was made at a nursery in La Menitre, Maine Et Loire, France.

Asexual reproduction of the new cultivar 'MINSYBV3S01' was first performed in February 2011 in La Menitre, Maine Et Loire, France, by softwood cuttings. Subsequent propagation has shown that the unique features of this cultivar are stable and reproduced true to type in 12 successive generations.

SUMMARY OF THE INVENTION

The cultivar 'MINSYBV3S01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYBV3S01'. These characteristics in combination distinguish 'MINSYBV3S01' as a new and distinct *Hibiscus* cultivar:

1. Large flowers.
2. Attractive violet-blue flowers with a small maroon eye.
3. Upright habit.

PARENT COMPARISON

Plants of the new cultivar 'MINSYBV3S01' are similar to plants of the seed parent variety in most horticultural characteristics, however, plants of the new cultivar 'MINSYBV3S01' differ in the following;

1. The new variety is more freely-branching than the seed parent.
2. The new variety has violet-blue flowers with maroon centers, while the seed parent has darker purple flowers with a blue spot.
3. Flowers of the new variety are larger than those of the seed parent.

COMMERCIAL COMPARISON

Plants of the new cultivar 'MINSYBV3S01' can be compared to the variety *Hibiscus syriacus* 'DVPazurri', U.S. Plant Pat. No. 20,563. These varieties are similar in most horticultural characteristics however, 'MINSYBV3S01' differs in the following:

1. Flowers of the new variety are darker violet-blue than this comparator.
2. Flowers of the new variety are larger than this comparator.

BRIEF DESCRIPTION OF THE PHOTOGRAPHS

Figure 1:
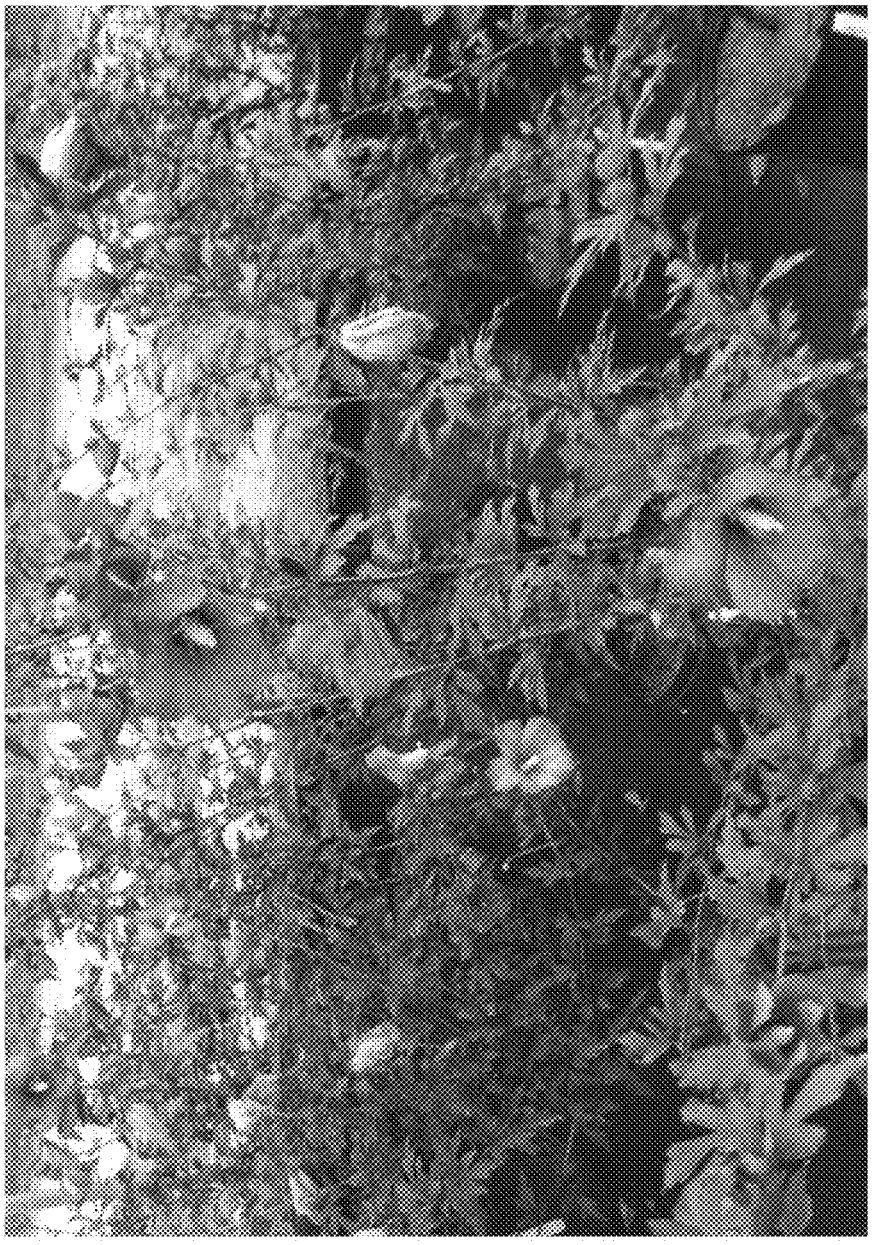

The accompanying photograph in FIG. 1 illustrates in full color a typical plant of 'MINSYBV3S01' grown in a 3 gallon pot, in Grand Haven, Mich.

Figure 2:
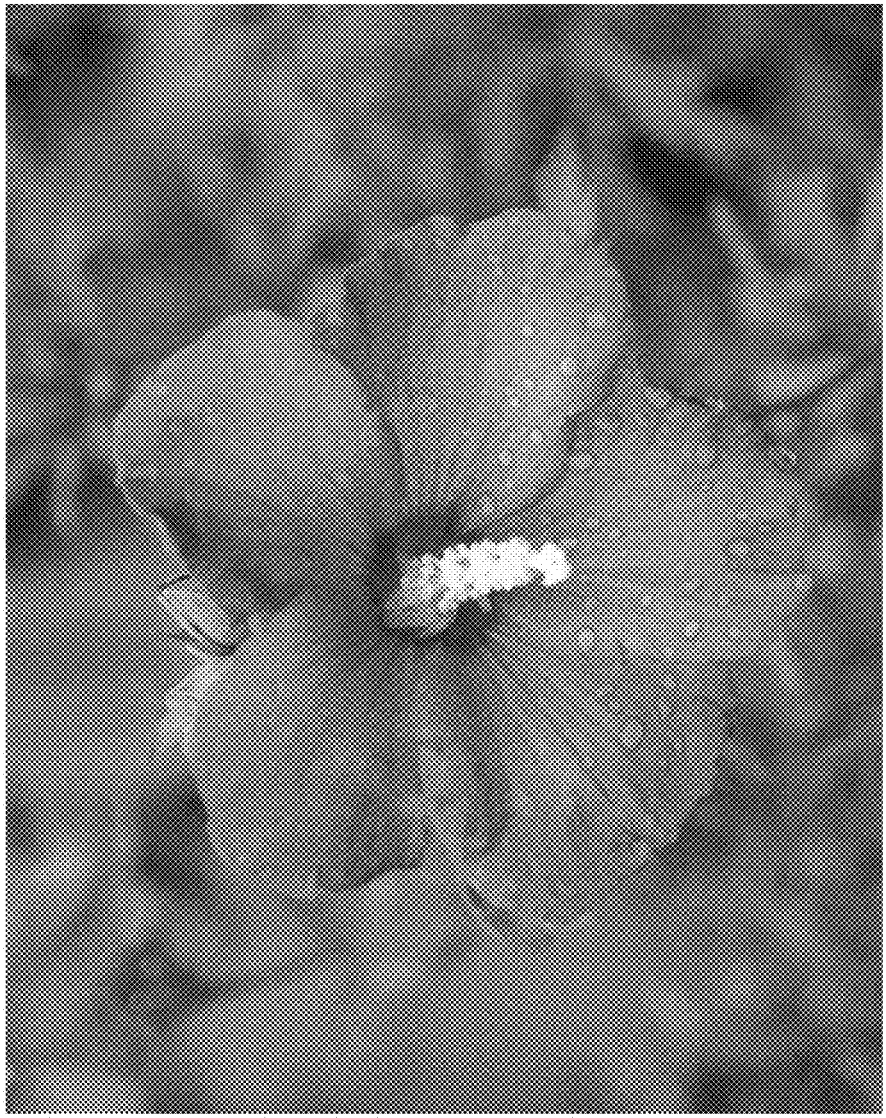

FIG. 2 illustrates in full color a typical flower of 'MINSYBV3S01'. Age of the plant photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6th edition, except where general terms of ordinary dictionary significance are used. The following observations and measurements describe 'MINSYBV3S01' plants grown in a poly-greenhouse in Grand Haven, Mich., under natural lighting. Measurements were taken in July 2018. The plants were 2-3 years old in 3 gallon containers. The growing temperature ranged from approximately −5° C. to 27° C. Measurements and numerical values represent averages of typical plant types.

Botanical classification: *Hibiscus syriacus* 'MINSYBV3S01'.

PROPAGATION

Time to initiate roots: 20 days at approximately 25° C.

Time to produce a rooted young plant: About 90 days at 25° C.

PLANT

Plant type: Upright flowering perennial shrub.
Age of plant described: Approximately 3 years old.
Overall plant shape: Upright, somewhat columnar.
Growth habit: Upright, slightly outward.
Height: 58 cm.
Spread: 37 cm.
Growth rate: Moderate.
Plant vigor: Good.
Branching characteristics: Basal.
Quantity of primary branches: 5.
Characteristics of primary lateral branches:
- *Length.*—36 cm.
- *Diameter.*—8 mm.
- *Shape.*—Round.
- *Aspect.*—0-45°.
- *Strength.*—Good.
- *Color.*—New: RHS Green 138A. Woody: RHS Brown 200A.
- *Pubescence.*—On new growth.

Internode length: 1.75 cm.
Root description: Fibrous, medium root thickness. Tan/brown in color, not effectively measured with a color chart.

FOLIAGE

Leaf:
- *Arrangement.*—Single.
- *Average length.*—5.25 cm.
- *Average width.*—3 cm.
- *Shape of blade.*—Overall ovate, with 3 deep lobes.
- *Apex.*—Acute.
- *Base.*—Oblique.
- *Margin.*—Lobed.
- *Texture of top surface.*—Slightly rough, ribbed.
- *Texture of bottom surface.*—Rough, distinct veins.
- *Pubescence.*—None.
- *Variegation.*—None.
- *Color.*—Young foliage upper side: RHS Green 149A and 149C, both colors present individually. Young foliage under side: RHS Green 143C. Mature foliage upper side: RHS Green 143A. Mature foliage under side: RHS Green 143B.
- *Venation.*—Type: Palmate. Venation color upper side: RHS Green 143C. Venation color under side: RHS Green 144D.
- *Petiole.*—Length: 1 cm. Diameter: 2 mm. Pubescence: Pubescent, both sides. Color: RHS Green 143A, both sides.

FLOWER

Natural flowering season: Summer.
Flower arrangement: Axillary, single.
Flower shape: Rotate.
Flowering habit: Whorl.
Quantity of flowers per lateral stem: 6.
Quantity of buds per lateral stem: 6.
Quantity of flowers and buds per plant: About 50.
Persistent or self-cleaning: Self-cleaning.

Bud:
- *Shape.*—Oval.
- *Length.*—2.5 cm.
- *Diameter.*—1.5 cm.
- *Color.*—RHS Green 143B.

Flower:
- *Diameter.*—12 cm.
- *Depth.*—7 cm.
- *Aspect.*—Outward.
- *Shape.*—Rotate.

Petals:
- *Quantity.*—5.
- *Appearance.*—Delicate with slightly undulate edges.
- *Arrangement.*—Whorled, moderately overlapping.
- *Attitude outermost petal.*—Moderately ascending.
- *Length.*—6 cm.
- *Width.*—5.5 cm.
- *Shape.*—Obovate.
- *Apex.*—Obtuse.
- *Base.*—Attenuate.
- *Margin.*—Undulate.
- *Texture, upper and lower surfaces.*—Smooth, soft.
- *Color.*—Overall Violet to Violet Blue with a small maroon eye. When opening, upper surface: RHS Violet 86A and N87A. When opening, lower surface: RHS Violet 86A and N87A. Fully opened, upper surface: RHS Violet-Blue 93B, blended to Purple-Violet N80B. Eye Purple N79B and C. The eye zone is small, coloration is extended minimally, about 10% of the petal length. Fully opened, lower surface: RHS Violet-Blue 93B blended with Purple 75B.

Petaloids: None.

Sepals:
- *Arrangement.*—Radial.
- *Quantity.*—5.
- *Length.*—2.5 cm.
- *Width.*—2 mm.
- *Shape.*—Narrowly triangular.
- *Margin.*—Entire.
- *Apex.*—Narrowly acute.
- *Base.*—Truncate. Color, mature: Upper sides: RHS Green 143C. Under side: RHS Green 143D.
- *Texture.*—Smooth, both sides.

Calyx:
*Shape*.—Funnelform.
*Length*.—2.5 cm.
*Diameter*.—7.5 cm.
Peduncles:
*Length*.—2.25 cm.
*Diameter*.—3 mm.
*Angle*.—15-45°.
*Strength*.—Good.
*Texture*.—Pubescent.
*Color*.—RHS Green 143B.
Pedicels: None.
Fragrance: None.

REPRODUCTIVE ORGANS

Stamens:
*Number*.—50.
*Filament length*.—2 mm.
*Filament color*.—RHS Green-White 157D.
Anthers:
*Shape*.—Fused.
*Length*.—2 mm.
*Color*.—RHS White 155A.
*Pollen color*.—RHS White 155A.
*Pollen amount*.—Moderate.
Pistil: Fused with 5 protruding stigma from the top.
*Number*.—1.
*Length*.—4.25 cm.
*Style*.—Length: 3.7 cm. Color: RHS White 155C
*Stigma*.—Shape: Peltate. Color: RHS White 155A.
*Ovary color*.—RHS White 155C with light shading of Red-Purple 60B.

OTHER CHARACTERISTICS

Seeds and fruits: None observed.
Disease/pest resistance: Neither resistance nor susceptibility to normal diseases and pests of *Hibiscus* have been observed.
Garden performance: Good tolerance, performs well in humid conditions.
Temperature tolerance: Low temperature tolerance to at least USDA Zone 4, high temperature tolerance to at least 40° C.

What is claimed is:

1. A new and distinct cultivar of *Hibiscus* plant named 'MINSYBV3S01' as herein illustrated and described.

* * * * *